United States Patent [19]

Siemer

[11] 4,313,752
[45] Feb. 2, 1982

[54] 2,2-DIMETHYLVALERIC ACID FOR GROWTH ENHANCEMENT OF SUGARCANE

[75] Inventor: Sidney R. Siemer, Fresno, Calif.
[73] Assignee: W. R. Grace & Co., New York, N.Y.
[21] Appl. No.: 181,731
[22] Filed: Aug. 26, 1980
[51] Int. Cl.$^3$ ............................................ A01N 37/00
[52] U.S. Cl. ........................................ 71/27; 71/113; 127/42
[58] Field of Search .................. 71/64.12, 27, 1, 11, 71/76, 88, 94, 106, 107, 113, 115; 127/42

[56] References Cited

U.S. PATENT DOCUMENTS 3,870,503  3/1975  Nickell .............................. 71/106
4,284,425  8/1981  Luteri ................................. 71/27

Primary Examiner—S. Leon Bashore
Assistant Examiner—Ferris H. Lander
Attorney, Agent, or Firm—Charles L. Harness

[57] ABSTRACT

Treatment of sugarcane with 2,2-Dimethylvaleric acid enhances growth.

8 Claims, No Drawings

2,2-DIMETHYLVALERIC ACID FOR GROWTH ENHANCEMENT OF SUGARCANE

This invention is directed to applying 2,2-dimethylvaleric acid to sugarcane, thereby to cause growth enhancement in the sugarcane.

U.S. Pat. No. 3,870,503 shows the use of n-valeric acid to increase sucrose yield in sugarcane a few weeks prior to harvest. So far as is known, however, n-valeric acid causes little or no growth enhancement. Tests with various other valeric acid homologs, salts, and derivatives also show little or no growth enhancement, e.g., with sodium valerate, ammonium valerate, and ethylvaleric acid. The latter actually causes growth reduction. It is not possible to predict whether a given valeric acid derivative will cause growth enhancement.

SUMMARY OF THE INVENTION

According to the present invention the desired objectives have been achieved by the application of a growth-enhancing composition comprising 2,2-dimethylvaleric acid. More specifically, an excellent increase in growth has been obtained by applying a spray or dust comprising said material to sugarcane stalks and leaves in a crop which is 1–36 months old. The composition is applied directly to the stalks and leaves, by spraying, dusting or the like in order that it be deposited on the stalks and leaves including the younger, growing parts thereof. Experimentally, it can be applied by injection into the spindle.

As is well known, the normal maturation cycle of sugarcane can vary considerably depending on local conditions, from less than 1 year to 3 years or more. For instance, under conditions such as those prevailing in Hawaii sugarcane is normally ripe for harvesting when about 18 to 36 months of age while in other areas of the world sugarcane can be only 9 to 12 months of age when harvested.

The preferred usage form is a mixture containing 2,2-dimethylvaleric acid in an aqueous solution or suspension utilizing one or a combination of known surface active agents commonly and variously used in the prior art as wetting agents, detergents or emulsifying agents.

In accordance with this invention, a sugarcane crop which is nearing normal growth reduction due to temperature is treated with 2,2-dimethylvaleric acid as herein defined or with a composition containing same.

Good results are obtained when the sugarcane crop is treated at a rate in the range of from 1 to 10 pounds of a 2,2-dimethylvaleric acid (active ingredient, ai, or A.I.) or equivalent A.I.-containing composition per acre of sugarcane. However, higher rates (e.g., up to about 30 pounds of A.I or more per acre) or rates lower than 1 pound per acre can also be used. The optimum amount will vary somewhat depending on the particular mode of application, environmental conditions, time of year, and age and variety of cane being treated, but can readily be determined for each particular case by preliminary testing. Application is generally made to plants 1 to 36 months old.

The A.I. is conveniently applied in the field in the form of an aqueous solution, emulsion or suspension, i.e., in a liquid composition which may be sprayed onto the maturing cane plants from a boom-sprayer, or an airplane, or it can be dusted on from an airplane or tha like as a dust composition which contains the active compound diluted with an inert solid such as clay.

In preparing suitable liquid composition, surface active agents of the type described, for instance, in U.S. Pat. No. 3,224,865, column 2, lines 61–66 or in U.S. Pat. No. 3,245,775, column 2, lines 57–64 are convenient to use. The preferred surfactants for use in liquid compositions of the present invention are those of the non-ionic type, e.g., alkyl phenoxy poly(ethyleneoxy)ethanols such as adducts of nonylphenol and ethylene oxide; trimethyl nonyl polyethylene glycol ethers; polyethylene oxide adducts of fatty and resin acids, and long chain alkyl mercaptan adducts with ethylene oxide. The surfactant (surface active agent) is not critical.

With the type of spray apparatus used in this work, it has been found convenient to apply the A.I. to the sugarcane field in the form of an aqueous solution, suspension or emulsion having a concentration of A.I. such that the application at the rate of from 1 to 60 gallons of liquid composition per acre will provide the required dosage of A.I. However, the use of lower or higher gallonages may be preferred when a different dispensing mechanism is used.

The preferred carrier for the A.I. is water to which about 0.1 to 2 percent by weight of surface active agent has been added. However, instead of using water as the carrier, non-phytotoxic mineral oils either as such or in the form of water-in-oil or oil-in-water emulsions may be used similarly in accordance with practices which are otherwise well known in the art of treating vegetation in the field with beneficial growth control agents. Excellent results are obtained when the A.I. is present as essentially the sole active ingredient in the treating composition, but it may also be applied in combination with other sugarcane treating materials.

A preferred composition consists essentially of
(a) 2,2-dimethylvaleric acid, about 0.6 to 50 wt. %
(b) about 0.1 to 2 wt. % of a nonionic surface active agent, and
(c) balance, water, to make 100%.

Testing Procedure

A moving belt spray chamber in a greenhouse was calibrated to deliver 30 gal. of spray/acre. 2,2-dimethylvaleric acid was weighed out to give rate equivalents of 1, 10, and 100 mg/plant. These rates correspond to approximately 4 lbs./acre, 0.4 lbs./acre and 0.04 lbs./acre. These rates are all expressed in terms of active ingredient.

Plants were treated in groups of three. Individual plants were oriented such that the leaves were parallel to the belt and thus all foliage was exposed to the spray mist in a uniform manner. The three individual plants previously selected for uniformity were placed on an aluminum panel so that all three plants moved through the spray as a single unit. The belt speed was calibrated at 3 mph with the spray nozzle spraying perpendicular to the belt and at 90° to the direction of travel.

The plants, after being sprayed, were placed in a pattern on the greenhouse floor with no contact between plants. After the plants were dry they were grouped on the greenhouse table. There was foliage contact between plants treated with the three rates of the test compound. Watering of the treated plants was effected so that there was minimal re-wetting of the sprayed foliage.

Measurements were made immediately after the plants were placed on the table by laying a pot label across the top of the pot and measuring from it to the first visible dewlap. Measurements were made at 0 time, 1 and 2 weeks after treatment. Data are presented showing growth for one week and two weeks.

The averages of the three measurements in Table 1 were divided by the corresponding control average to give the T/C Ratios. It will be noted that the additive gave increased growth, as compared to the control group, in all six instances.

TABLE 1

Evaluation of 2,2-dimethylvaleric acid, applied as spray, on growth rate of 2-month old setts of sugarcane variety CL-41-233. (average of 3 replications)

| Rate, conc. ppm | R/C Ratios*, Avg. growth rate/day | |
|---|---|---|
| | 1 wk. | 2 wks. |
| 3.3 | 3.045 | 1.808 |
| 33.3 | 4.074 | 1.476 |
| 333.0 | 1.445 | 1.046 |

*T/C Ratios = growth/day-treated/growth/day-check (untreated).

The summary of growth enhancement effects obtained from applications of 2,2-dimethylvaleric acid at two sites in Florida are shown in Table 2. All three applications of 2,2-dimethylvaleric acid caused growth enhancement over untreated tissue. Comparison of 2,2-dimethylvaleric acid with a long known growth enhancing material, Gibberellic acid, showed 2,2-dimethylvaleric acid to have approximately ⅛ as much activity.

TABLE 2

Summary of growth enhancement effects obtained from applications of the following treatments made into the spindles of individual sugarcane plants (var. CL-41-223), application made using 3 ml total solution.

| Treatment | Rate mg/plant | Site I Avg Cm growth | Site I % of untreated | Site II Avg Cm growth | Site II % of untreated |
|---|---|---|---|---|---|
| Gibberellic acid | 1.0 | 16.05 | 730 | 19.28 | 3012 |
| | 0.1 | 6.25 | 284 | 9.88 | 1544 |
| | 0.01 | 13.00 | 591 | 12.92 | 2019 |
| Round-up | 1.0 | −0.18 | 0 | 0.16 | 25 |
| Gibberellic acid + Roundup | 0.01 + 1.0 | −0.18 | 0 | 0.38 | 59 |
| | 0.1 + 1.0 | −1.09 | 0 | 7.50 | 1172 |
| | 1.0 + 1.0 | 0.55 | 25 | 6.84 | 1013 |
| 2,2-Dimethyl-valeric acid | 0.01 | — | — | 2.56 | 400 |
| | 0.1 | — | — | 1.56 | 244 |
| | 1.0 | — | — | 1.46 | 228 |
| Untreated | 0 | 2.20 | 100 | 0.64 | 100 |

The average of three measurements obtained from foliar spray applications of sugarcane treated with 2,2dimethylvaleric acid are shown in Table 3. A five fold increase was obtained over the untreated plants and 2,2-dimethylvaleric acid in combination with the growth regulator Glyphosate (isopropyl-amine salt of n-phosphonomethylglycine) showed a three fold increase over untreated tissue. This Glyphosate growth increase in combination with the growth regulator Glyphosate was especially interesting and totally unexpected. Growth enhancement by 2,2-dimethylvaleric acid following Glyphosate treatment was more than twice that obtained with the Gibberellic acid Glyphosate treatment. In the table, "ai/A" means active ingredient per acre.

TABLE 3

Summary of growth enhancement effects obtained from the following treatments made by foliar spray application to sugarcane plants (var. CL-41-223). Application made using 60 gpa.

| Treatment | Rate lbs ai/A | Site I Avg Cm growth | Site I % of untreated | Site II Avg Cm growth | Site II % of untreated |
|---|---|---|---|---|---|
| Gibberellic acid | 0.12 | 5.53 | 251 | 8.74 | 1366 |
| Gibberellic acid + Roundup | 0.12 0.5 | 2.42 | 110 | 0.73 | 114 |
| 2,2-Dimethyl-valeric acid | 4.0 8ppm | — | — | 3.30 | 516 |
| 2,2-Dimethyl-valeric acid + Roundup | 4.0 0.5 | — | — | 2.05 | 320 |
| Roundup | 0.5 | 0.64 | 29 | 0.15 | 23 |
| Untreated | 0 | 2.20 | 100 | 0.64 | 100 |

I claim:

1. A process for enhancing growth in sugarcane plants which comprises applying to the plant, 2,2-dimethylvaleric acid at a dosage rate per acre of 1 to 10 lbs.

2. A process according to claim 1 wherein the 2,2-dimethylvaleric acid is sprayed onto the cane plants as a liquid composition containing water as a carrier.

3. A process according to claim 2 wherein the aqueous composition contains a surface active agent.

4. A process according to claim 2 wherein the 2,2-dimethylvaleric acid is applied to the cane plants as an aqueous solution or suspension at the rate of about 1 to 60 gallons of aqueous composition per acre.

5. A process according to claim 4 wherein the cane plants are between 1 and 36 months of age when the 2,2-dimethylvaleric acid is applied.

6. A process according to claim 5 wherein the aqueous composition contains about 0.6 to 50 percent weight of 2,2-dimethylvaleric acid.

7. Method according to claim 1, in which the 2,2-dimethylvaleric acid application follows a prior application of a growth regulating amount of the isopropyl amine salt of n-phosphonomethylglycine, whereby the 2,2-dimethylvaleric acid reduces the growth-stopping effect of the said isopropylamine salt.

8. Sugarcane treating composition consisting essentially of
(a) 2,2-dimethylvaleric acid, about 1 to 50 wt %;
(b) about 0.1 to 2 wt. % of a nonionic surface active agent, and
(c) balance, water, to make 100%.

* * * * *